United States Patent [19]

Lee

[11] Patent Number: 4,647,460
[45] Date of Patent: Mar. 3, 1987

[54] COMPOSITION AND METHOD FOR NARCOTICS WITHDRAWAL

[76] Inventor: Jeoungkyu Lee, Fujisawa-City, Kanagawa-Ken, Japan

[21] Appl. No.: 773,384

[22] Filed: Sep. 6, 1985

[51] Int. Cl.⁴ ............................................. A61K 35/78
[52] U.S. Cl. ................................... 424/195.1; 514/812
[58] Field of Search ...................... 424/195.1; 514/812

[56] References Cited

U.S. PATENT DOCUMENTS 4,569,843  2/1986  Kim ................................... 424/195.1

Primary Examiner—Donald B. Moyer
Assistant Examiner—John W. Rollins, Jr.
Attorney, Agent, or Firm—Townsend and Townsend

[57] ABSTRACT

Physical and emotional symptoms characteristic of withdrawal from narcotics addiction are reduced or eliminated entirely by treatment with a unique combination of naturally-derived ingredients, primarily herbal in origin, the component of highest concentration being Ginseng radix. Other components of the composition include Amanae bulbus, Puchrestrae radix, Euphorbiae pekinensis, Lathyridis semen, Auicular margark feral, Manis squama, Zizyphi spinosi semen, Angelicae gigantis radix, Cnidii rhizoma, Rehmaniae radix and Paeoniae radix. The composition is administered internally, preferably orally, to the subject upon cessation of narcotics intake, with the result that most of the symptoms normally associated with such withdrawal are severely reduced in intensity.

9 Claims, No Drawings

COMPOSITION AND METHOD FOR NARCOTICS WITHDRAWAL

BACKGROUND OF THE INVENTION

The present invention relates to narcotics addiction, and particularly to treatments for easing the physical and emotional symptoms attendant upon narcotics withdrawal.

Narcotics addiction is the unfortunate result not only of drug abuse but also of a variety of human hardship situations, severely reducing the quality of life of those addicted as well as their ability to contribute to society. One of the best known treatments is the use of methadone hydrochloride as a substitute for the narcotic during withdrawal. Unfortunately, the physical discomfort and emotional unrest normally associated with the drug originally giving rise to the addiction has been found to recur upon discontinuing the administration of methadone. In addition, it has been found that the volume of methadone required to overcome the withdrawal symptoms arising from the original drug gradually increases as a patient continues to use the methadone, as does the tendency to become addicted to methadone itself.

SUMMARY OF THE INVENTION

It has now been discovered that a unique combination of herbal ingredients, none of which are addictive, has the capability of reducing and ultimately eliminating most if not all of the unpleasant withdrawal symptoms when administered to a narcotics addict upon cessation of narcotics intake. The effect is seen in a wide range of symptoms, ranging from physical manifestations and discomfort to emotional unrest, and including the various bodily symptoms such as the circulatory, nervous and digestive systems.

DETAILED DESCRIPTION OF THE INVENTION

The composition of the present invention contains a combination of active ingredients, all naturally derived and primarily herbal in origin. The ingredients are as follows:
 (a) *Ginseng radix*
 (b) *Amanae bulbus*
 (c) *Puchrestrae radix*
 (d) *Euphorbiae pekinensis*
 (e) *Lathyridis semen*
 (f) *Auicular margark feral*
 (g) *Manis squama*
 (h) *Zizyphi spinosi semen*
 (i) *Angelicae gigantis radix*
 (j) *Cnidii rhizoma*
 (k) *Rehmaniae radix*
 (l) *Paeoniae radix*

The amount of each ingredient as a proportion of the whole may vary, although certain proportions are preferred—namely, the *Ginseng radix* preferably comprises about 20% to about 30% by weight; the *Amanae bulbus, Puchrestrae radix, Euphorbiae pekinensis,* and *Lathyridis semen* each individually comprise about 10% to about 20% by weight; the *Zizyphi spinosi semen, Angelicae gigantis radix,* the *Cnidii rhizoma,* and *Rehmaniae radix* and the *Paeoniae radix* each individually comprise about 3% to about 10% by weight; and the *Auicular margark feral* and the *Manis squama* each comprise from about 0.05% to about 1.0% by weight, all weight percents based on total active ingredients. In fact, a composition having the following amounts, based on a 250 mg total, has been found to be particularly effective:
 *Ginseng radix:* 60 mg
 *Amanae bulbus:* 45 mg
 *Puchrestrae radix:* 25 mg
 *Euphorbiae Pekinensis:* 32.5 mg
 *Lathyridis semen:* 25 mg
 *Auicular margark feral:* 0.175 mg
 *Manis squama:* 2.325 mg
 *Zizyphi spinosi semen:* 18.75 mg
 *Angelicae gigantis radix:* 9.375 mg
 *Cnidii rhizoma:* 9.375 mg
 *Rehmaniae radix:* 11.25 mg
 *Paeoniae radix:* 11.25 mg While the composition may be administered in any convenient form, it is preferably combined prior to consumption as an intimate mixture, by grinding the components together to a powdered consistency, or liquifying them as a suspension or solution. The composition may then be consumed in liquid or solid form. For purposes of treatment, the composition is taken internally, preferably orally.

The composition may be rendered in a form which provides slow release to the digestive system. Capsules and encapsulated embodiments are particularly convenient in this regard.

The dosage may vary depending on the level of narcotic intake prior to withdrawal, and hence the severity of the withdrawal symptoms, as well as the size and physical condition of the patient. In most cases, a quantity ranging from about 0.5 to about 20 grams per day, preferably from about 1 to about 10 grams per day, in each case based upon the aggregated active ingredients. Administration of the composition is preferably achieved by dividing the daily dosage into small portions taken at equally spaced intervals throughout the day. About 2 to about 10 portions per day, preferably about 4 to about 6, will generally provide the best results.

The composition may be combined with or taken in conjunction with other treatments or medicaments, such as tranquilizers, sleep-promoting agents and the like. The treatment is applicable to narcotic or opiate addiction in general, and particularly to heroin or morphine addiction.

The active ingredients are known naturally derived species, primarily herbal, readily obtainable from natural sources by conventional methods.

The following examples are offered for illustrative purposes only, and are intended neither to limit nor define the invention in any manner.

EXAMPLES

Twenty male patients under treatment for heroin addiction in the Psychoneurologic Department of PRAMONGKUT KLAO Army Hospital in Bangkok, Thailand were tested. The age distribution of the patients was as follows:

TABLE 1

| Age Distribution of Patients | |
|---|---|
| Age Range (years) | Number of Patients |
| Below 20 | 1 |
| 20–25 | 13 |
| 26–30 | 3 |
| 31–35 | 1 |
| 36–40 | 1 |
| 41–45 | 1 |

TABLE 1-continued

| Age Distribution of Patients | |
|---|---|
| Age Range (years) | Number of Patients |
| Total: | 20 |

The distribution among the patients of the duration of heroin abuse prior to treatment was as follows:

TABLE 2

| Abuse Duration Distribution | |
|---|---|
| Duration | Number of Patients |
| 6 months–1 year | 4 |
| 2–5 years | 11 |
| 6 years or more | 5 |
| Total: | 20 |

The rate of heroin consumption per patient prior to treatment was distributed as follows:

TABLE 3

| Consumption Rate Distribution | |
|---|---|
| Quantity per Day | Number of Patients |
| Approximately 30 mg | 8 |
| 40–100 mg | 10 |
| 150–200 mg | 1 |
| Above 200 mg | 1 |
| Total: | 20 |

Capsules containing the following active ingredients were used for treatment:

TABLE 4

| Treatment Composition | | |
|---|---|---|
| Ginseng radix | 60 | mg |
| Amanae bulbus | 45 | mg |
| Puchrestrae radix | 25 | mg |
| Euphorbiae pekinensis | 32.5 | mg |
| Lathyridis semen | 25 | mg |
| Auicular margark feral | 0.175 | mg |
| Manis squama | 2.325 | mg |
| Zizyphi spinosi semen | 18.750 | mg |
| Angelicae gigantis radix | 9.375 | mg |
| Cnidii rhizoma | 9.375 | mg |
| Rehmaniae radix | 11.25 | mg |
| Paeoniae radix | 11.25 | mg |
| Total: | 250 | mg |

The patients were each administered four capsules four times per day over a fourteen-day period. The patients were examined by observation on the seventh and fourteenth days for a series of symptoms, with the results listed below in Tables 5 and 6.

TABLE 5

| | Incidence of Withdrawal Symptoms After Seven Days | | |
|---|---|---|---|
| Symptom | Number of Patients Not Experiencing Symptom | Number of Patients Experiencing Symptom to Moderate Degree | Number of Patients Experiencing Symptom to Extreme Degree |
| Lacrimation | 11 | 9 | 0 |
| Rhinorrhea | 19 | 1 | 0 |
| Yawning | 12 | 8 | 0 |
| Goose flesh | 13 | 7 | 0 |
| Perspiration | 12 | 8 | 0 |
| Restlessness | 14 | 6 | 0 |
| Chills | 17 | 3 | 0 |
| Abdominal pain | 17 | 3 | 0 |
| Diarrhea | 18 | 2 | 0 |
| Vomiting | 19 | 1 | 0 |
| Body weakness | 9 | 11 | 0 |
| Anorexia | 14 | 6 | 0 |
| Sleep disturbances | 17 | 3 | 0 |
| Anxiety | 13 | 7 | 0 |
| Leg muscle spasms | 14 | 6 | 0 |
| Joint pains | 12 | 8 | 0 |

TABLE 6

| | Incidence of Withdrawal Symptoms After Fourteen Days | | |
|---|---|---|---|
| Symptom | Number of Patients Not Experiencing Symptom | Number of Patients Experiencing Symptom to Moderate Degree | Number of Patients Experiencing Symptom to Extreme Degree |
| Lacrimation | 20 | 0 | 0 |
| Rhinorrhea | 20 | 0 | 0 |
| Yawning | 16 | 4 | 0 |
| Goose flesh | 20 | 0 | 0 |
| Perspiration | 17 | 3 | 0 |
| Restlessness | 18 | 2 | 0 |
| Chills | 20 | 0 | 0 |
| Abdominal pain | 18 | 2 | 0 |
| Diarrhea | 20 | 0 | 0 |
| Vomiting | 19 | 1 | 0 |
| Body weakness | 13 | 7 | 0 |
| Anorexia | 13 | 7 | 0 |
| Sleep disturbances | 20 | 0 | 0 |
| Anxiety | 14 | 6 | 0 |
| Leg muscle spasms | 14 | 6 | 0 |
| Joint pains | 17 | 3 | 0 |

What is claimed is:

1. A composition of matter in unit dosage form comprising a combination of the following at weight percents within the ranges shown:
   (a) Ginseng radix, 20% to 30%;
   (b) Amanae bulbus, 10% to 20%;
   (c) Puchrestrae radix, 10% to 20%;
   (d) Euphorbiae pekinensis, 10% to 20%;
   (e) Lathyridis semen, 10% to 20%;
   (f) Auicular margark feral, 0.05% to 1.0%;
   (g) Manis squama, 0.05% to 1.0%;
   (h) Zizyphi spinosi semen, 3% to 10%;
   (i) Angelicae gigantis radix, 3% to 10%;
   (j) Cnidii rhizoma, 3% to 10%;
   (k) Rehmaniae radix, 3% to 10%;
   (l) Paeoniae radix, 3% to 10%.

2. A composition in accordance with claim 1 in which the weight percents of said substances in said composition are as follows:
   (a) 24.0
   (b) 18.0
   (c) 10.0
   (d) 13.0
   (e) 10.0
   (f) 0.07
   (g) 0.9

(h) 7.5
(i) 3.8
(j) 3.8
(k) 4.5
(l) 4.5.

3. A method for reducing withdrawal symptoms in a patient suffering from addiction to an opiate, comprising administering orally 0.5 to about 20 grams per day to said patient the composition of claim 1.

4. A method for reducing withdrawal symptoms in a patient suffering from heroin addiction, comprising administering orally 0.5 to about 20 grams per day to said patient the composition of claim 1.

5. A method in accordance with claim 4 in which the weight percents of said substances in said composition are as follows:
(a) 24.0
(b) 18.0
(c) 10.0
(d) 13.0
(e) 10.0
(f) 0.07
(g) 0.9
(h) 7.5
(i) 3.8
(j) 3.8
(k) 4.5
(l) 4.5.

6. A method in accordance with claim 5 in which said composition is administered at a dosage of about 8 to about 10 grams per day in about 4 to about 6 portions per day.

7. A method in accordance with claim 4 in which said compostion is administered in capsule form.

8. A method in accordance with claim 4 in which said composition is administered at a dosage of about 1 to about 10 grams per day.

9. A method in accordance with claim 3 or 4 in which said composition is administered at a dosage of about 8 to about 10 grams per day in about 2 to about 10 portions per day.

* * * * *